United States Patent
Yang et al.

(10) Patent No.: US 9,823,176 B2
(45) Date of Patent: Nov. 21, 2017

(54) PARTICULATE MATTER SENSOR

(71) Applicant: Hyundai Motor Company, Seoul (KR)

(72) Inventors: Sang Hyeok Yang, Gyeonggi-do (KR); Yong Sung Lee, Gyeonggi-do (KR); Dong Gu Kim, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 56 days.

(21) Appl. No.: 15/143,415

(22) Filed: Apr. 29, 2016

(65) Prior Publication Data

US 2016/0370276 A1    Dec. 22, 2016

(30) Foreign Application Priority Data

Jun. 19, 2015 (KR) .................... 10-2015-0087711

(51) Int. Cl.
| | |
|---|---|
| *G01R 27/26* | (2006.01) |
| *G01N 27/62* | (2006.01) |
| *G01N 15/06* | (2006.01) |
| *F01N 11/00* | (2006.01) |
| *G01N 15/00* | (2006.01) |

(52) U.S. Cl.
CPC ......... *G01N 15/0656* (2013.01); *F01N 11/00* (2013.01); *G01N 15/0606* (2013.01); *F01N 2550/04* (2013.01); *F01N 2560/05* (2013.01); *F01N 2560/12* (2013.01); *G01N 2015/0046* (2013.01); *Y02T 10/47* (2013.01)

(58) Field of Classification Search
CPC ........... G01N 15/0606; G01N 15/0656; G01N 27/24; G01N 27/226; G01N 27/407
See application file for complete search history.

(56) References Cited

U.S. PATENT DOCUMENTS

| | | | |
|---|---|---|---|
| 4,307,061 | A  | 12/1981 | Sarholz |
| 6,971,258 | B2 | 12/2005 | Rhodes et al. |
| 7,081,154 | B2 | 7/2006  | Schulte et al. |
| 7,628,007 | B2 | 12/2009 | Kittelson et al. |
| 7,644,609 | B2 | 1/2010  | Reutiman et al. |
| 7,765,792 | B2 | 8/2010  | Rhodes et al. |
| 7,832,254 | B2 | 11/2010 | Guenschel et al. |
| 7,872,466 | B2 | 1/2011  | Dorfmueller et al. |
| 7,900,500 | B2 | 3/2011  | Krafthefer |

(Continued)

FOREIGN PATENT DOCUMENTS

| | | |
|---|---|---|
| JP | H0650939 A  | 2/1994 |
| JP | H0656386 B2 | 7/1994 |

(Continued)

*Primary Examiner* — Minh N Tang
(74) *Attorney, Agent, or Firm* — Mintz Levin Cohn Ferris Glovsky and Popeo, P.C.; Peter F. Corless

(57) ABSTRACT

A particulate matter sensor is provided. The particulate matter sensor includes a particulate matter detection unit that has first and second electrodes separately disposed on a substrate and configured to generate capacitance to correspond to a quantity of a particulate matter accumulated between the first and second electrodes. A signal generator is configured to generate a frequency signal that determines a resonant frequency by the capacitance. A detection result processor is configured to detect a signal magnitude of a predetermined reference frequency in the frequency signal and distinguishes an exhaust level of the particulate matter based on a change of the signal magnitude.

10 Claims, 8 Drawing Sheets

(56) References Cited

U.S. PATENT DOCUMENTS

| | | | |
|---|---|---|---|
| 7,963,106 B2 | 6/2011 | Schmidt et al. | |
| 7,966,862 B2 | 6/2011 | Gualtieri et al. | |
| 8,035,404 B2 | 10/2011 | Schnell et al. | |
| 8,176,768 B2 * | 5/2012 | Kondo | G01N 15/0656 73/23.33 |
| 8,640,526 B2 | 2/2014 | Di Miro et al. | |
| 8,736,284 B2 | 5/2014 | Aoki | |
| 8,770,016 B2 | 7/2014 | Uchiyama et al. | |
| 9,605,578 B1 * | 3/2017 | Qi | F01N 9/002 |
| 2007/0264158 A1 | 11/2007 | Schmidt et al. | |
| 2008/0047847 A1 | 2/2008 | Schmidt et al. | |
| 2011/0030451 A1 | 2/2011 | Roesch et al. | |
| 2011/0314899 A1 | 12/2011 | Di Miro et al. | |
| 2011/0320171 A1 | 12/2011 | Okayama et al. | |

FOREIGN PATENT DOCUMENTS

| | | |
|---|---|---|
| JP | 2010-151553 A | 7/2010 |
| JP | 2013-231627 A | 11/2013 |
| JP | 2014-159782 A | 9/2014 |
| KR | 10-2014-0052720 A | 5/2014 |
| KR | 10-1461873 B1 | 11/2014 |
| KR | 10-2015-0010218 A | 1/2015 |

\* cited by examiner

PARTICULATE MATTER SENSOR

CROSS-REFERENCE TO RELATED APPLICATION

This application claims priority to and the benefit of Korean Patent Application No. 10-2015-0087711 filed in the Korean Intellectual Property Office on Jun. 19, 2015, the entire contents of which are incorporated herein by reference.

BACKGROUND (a) Field of the Invention

The present invention relates to a particulate matter sensor.

(b) Description of the Related Art

Typically, enforcement of vehicle exhaust gas discharge regulations has resulted in restriction and reduction of permissible levels of exhaust gas discharge. For example, as a representative reference, an allowance value of nitrogen oxide (NOx), was decreased to about 0.4 g/kWh. Generally, a diesel engine generates exhaust flow that includes variable amounts of particulate matter (PM). Accordingly, to comply with more stringent requirement regulations, a vehicle that includes a diesel engine requires inclusion of a diesel particulate filter Diesel Particulate Filter (DPF) that reduces the exhaust flow and On-Board Diagnostics (OBD) that detects a malfunction of the DPF.

An OBD sensor is a sensor configured to detect a failure of a vehicle component that has an influence on exhaust gas discharge and configured to notify a user when a DPF has failed. For example, the OBD sensor includes a broadband temperature sensor, a differential pressure sensor, an oxygen sensor, a NOx sensor, and a Particulate Matter (PM) sensor. A recommended exhaust amount of a PM is typically less than about 0.009 g/km. Therefore, it is difficult to perform PM monitoring to satisfy the requirement with a differential pressure sensor that has already been utilized to monitor a PM exhaust amount. Accordingly, a PM sensor that more accurately measures a PM exhaust amount is required.

The above information disclosed in this section is merely for enhancement of understanding of the background of the invention and therefore it may contain information that does not form the prior art that is already known in this country to a person of ordinary skill in the art.

SUMMARY

The present provides a particulate matter sensor that may measure an exhaust amount of a particulate matter more accurately.

Accordingly to one aspect, an exemplary embodiment of the particulate matter sensor may include a particulate matter detection unit with first and second electrodes separately disposed on a substrate and configured to generate capacitance to correspond to a quantity of a particulate matter that accumulates between the first and second electrodes. A signal generator may be configured to generate a frequency signal that determines a resonant frequency by the capacitance. Further, a detection result processor may be configured to detect a signal magnitude of a predetermined reference frequency in the frequency signal and distinguish an exhaust level of the particulate matter based on a variation of the signal magnitude.

According to exemplary embodiments of the present invention, a particulate matter sensor may have an improved sensitivity while a detection time may be reduced for detection of a particulate matter exhaust amount.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION

Figure 1:
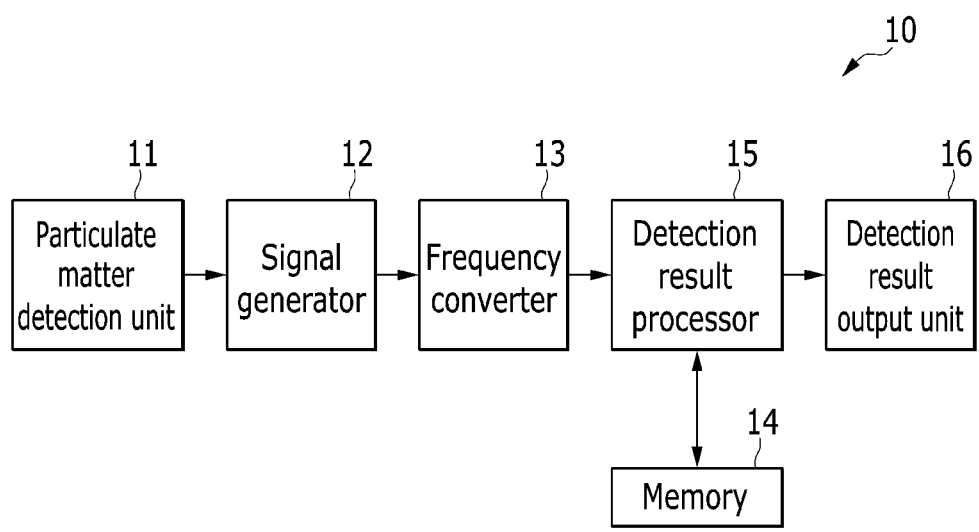
FIG. 1 is an exemplary block diagram illustrating a schematic configuration of a particulate matter sensor according to an exemplary embodiment of the present invention.

The present invention will be described more fully hereinafter with reference to the accompanying drawings in which exemplary embodiments of the invention are shown. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other exemplary embodiments, which may be included within the spirit and scope of the invention as defined by the appended claims.

Throughout this specification and the claims that follow, when it is described that an element is "coupled" to another element, the element may be "directly coupled" to the other element or "electrically coupled" to the other element through a third element.

It is understood that the term "vehicle" or "vehicular" or other similar term as used herein is inclusive of motor vehicle in general such as passenger automobiles including sports utility vehicles (SUV), buses, trucks, various commercial vehicles, watercraft including a variety of boats, ships, aircraft, and the like and includes hybrid vehicles, electric vehicles, combustion, plug-in hybrid electric vehicles, hydrogen-powered vehicles and other alternative fuel vehicles (e.g. fuels derived from resources other than petroleum).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. For example, in order to make the description of the present invention clear, unrelated parts are not shown and, the thicknesses of layers and regions are exaggerated for clarity. Further, when it is stated that a layer is "on" another layer or substrate, the layer may be directly on another layer or substrate or a third layer may be disposed there between.

Although an exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor. The memory is configured to store the modules and the processor is specifically configured to execute said modules to perform one or more processes which are described further below.

Furthermore, control logic of the present invention may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

Hereinafter, a particulate matter sensor according to an exemplary embodiment of the present invention will be described with reference to necessary drawings.

FIG. 1 is an exemplary block diagram illustrating a schematic configuration of a particulate matter sensor according to an exemplary embodiment of the present invention.

Figure 2:
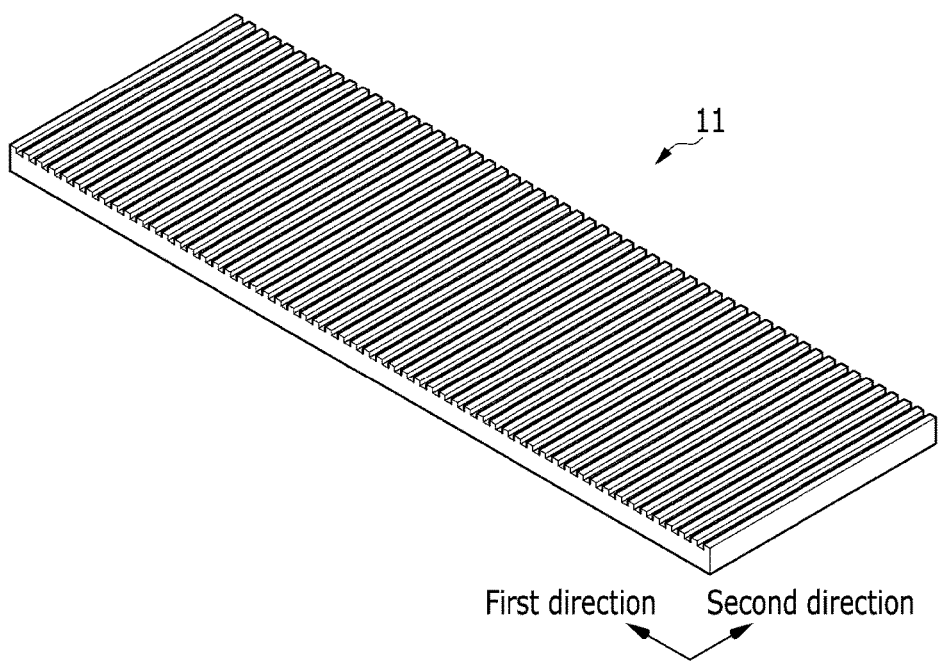
FIG. 2 is an exemplary schematic perspective view of a particulate matter detection unit according to an exemplary embodiment of the present invention.
Figure 3:
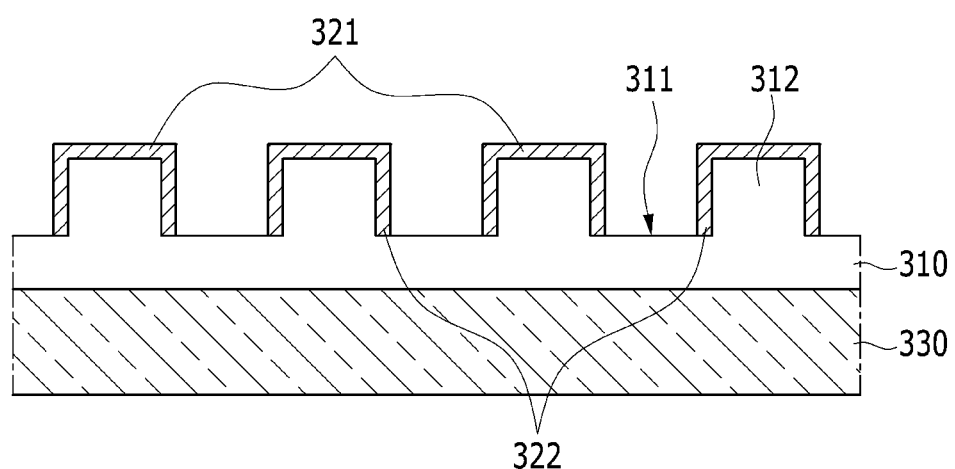
FIG. 3 is an exemplary cross-sectional view illustrating the particulate matter detection unit taken along a first direction of FIG. 2 according to an exemplary embodiment of the present invention.
Figure 4:
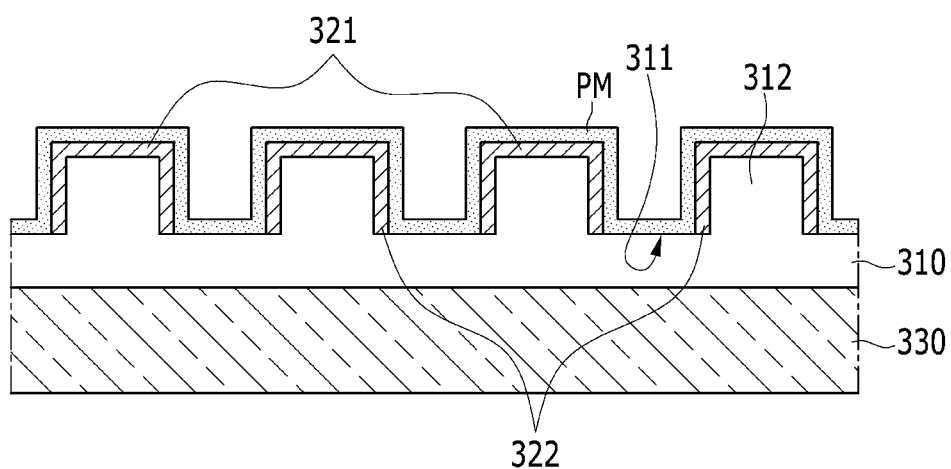
FIG. 4 is an exemplary cross-sectional view illustrating operation of a particulate matter detection unit in a particulate matter sensor according to an exemplary embodiment of the present invention.
Figure 5A:
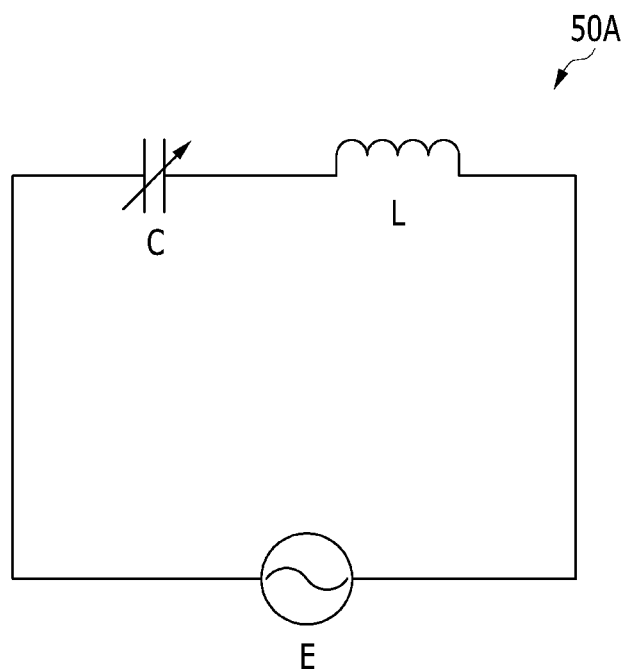
FIGS. 5A and 5B are exemplary diagrams illustrating examples of a resonant circuit constituting a signal generator in a particulate matter sensor according to an exemplary embodiment of the present invention.
Figure 5B:
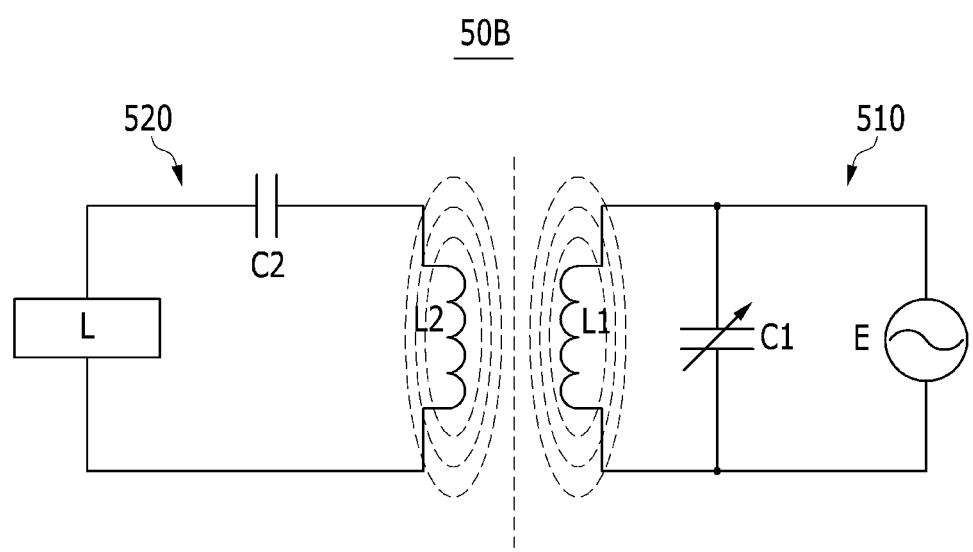

FIG. 2 is an exemplary schematic perspective view of a particulate matter detection unit according to an exemplary embodiment of the present invention. FIG. 3 is an exemplary cross-sectional view illustrating the particulate matter detection unit taken along a first direction of FIG. 2. FIG. 4 is an exemplary cross-sectional view illustrating operation of the particulate matter detection unit of FIG. 2. FIGS. 5A and 5B are exemplary diagrams illustrating examples of a resonant circuit constituting a signal generator according to an exemplary embodiment of the present invention.

Referring to FIG. 1, a particulate matter sensor 10 according to an exemplary embodiment of the present invention may include a particulate matter detection unit 11, a signal generator 12, a frequency converter 13, a memory 14, a detection result processor 15, and a detection result output unit 16. The various components of the sensor may be operated by a controller. The particulate matter detection unit 11 may be disposed within an exhaust line of a vehicle and may be configured to generate an electric signal that corresponds to a quantity (e.g., concentration) of a particulate matter included in the exhaust gas. In other words, the particulate matter detection unit 11 may be configured to vary the capacitance to correspond to a concentration of a particulate matter included in an exhaust gas.

Referring to FIGS. 2 and 3, the particulate matter detection unit 11 may include a substrate 310, first and second electrodes 321 and 322, and a protective substrate 330. The substrate 310 may be made of an insulating material. For example, the substrate 310 may be made of various insulating materials such as silicon, crystal, and glass. The first and second electrodes 321 and 322 may be disposed at a first surface of the substrate 310. The first and second electrodes 321 and 322 may extend from a surface of the substrate 310. The first and second electrodes 321 and 322 may extend in a second direction that intersects a first direction in which an exhaust gas flows in an exhaust line. The first and second electrodes 321 and 322 may be alternately disposed and separately disposed (e.g., spaced apart) by a predetermined gap. A groove 311 of a groove shape may be formed between the first and second electrodes 321 and 322. At the groove 311 formed between the first and second electrodes 321 and 322 a particulate matter may be included within an exhaust gas upon collection an accumulation.

The substrate 310 and the first and second electrodes 321 and 322 formed on the substrate 310 may be an Micro Electro Mechanical Systems (MEMS) structure shaped and patterned using Micro Electro Mechanical Systems (MEMS) technology. For example, as shown in FIG. 3, at a first surface of the substrate 310, a plurality of grooves 311 may be separated by a predetermined gap by a micro process that uses MEMS technology and a plurality of protruding portions 312 may enclose the plurality of grooves 311. The first and second electrodes 321 and 322 may form a conductive layer to cover the protruding portions 312 formed on the substrate 310. In other words, at one surface of the substrate 310, a conductive layer may be formed in the remaining portions, except for a lower surface of each groove 311 to form the electrodes 321 and 322 separately disposed by a predetermined gap.

Further, the first and second electrodes 321 and 322 may form a conductive pattern with a predetermined thickness on a flat surface of the substrate 310 by a micro process that uses MEMS technology. To protect a MEMS structure (e.g., the substrate 310 and the first and second electrodes 321 and 322) from an external impact, the protective substrate 330 may be coupled to a surface opposite to a surface where the first and second electrodes 321 and 322 are disposed in the substrate 310. The protective substrate 330 may be formed from a material with a predetermined strength level (e.g., ceramic or the like) and may be formed in a predetermined thickness to protect an MEMS structure from an external impact.

As shown in FIG. 4, the particulate matter detection unit 11 may include a capacitor formed by the first and second electrodes 321 and 322. The particulate matter (PM) may accumulate at the groove 311 between the first and second electrodes 321 and 322. Capacitance between the first and second electrodes 321 and 322 may vary based on a quantity of a PM that accumulates between the first and second electrodes 321 and 322. Therefore, the particulate matter sensor 10 according to an exemplary embodiment of the present invention may be configured to detect a concentration of a particulate matter in an exhaust gas based on capacitance between the first and second electrodes 321 and 322 of the particulate matter detection unit 11.

Referring again to FIG. 1, the signal generator 12 may be configured to generate a frequency signal that uses the capacitance in the particulate matter detection unit 11. The signal generator 12 may include a resonant circuit that may be configured to use capacitance that occurs in the particulate matter detection unit 11 and may be configured to generate a frequency signal using the resonant circuit.

Referring to FIG. 5A, a resonant circuit 50A may include the signal generator 12 with a driver E that may be configured to supply alternating current (AC) power, a coil L that may be configured to generate a magnetic field by AC power supplied from the driver E, and a capacitor C that may be connected to the coil L to determine a vibration frequency (e.g., resonant frequency) of a magnetic field. The capacitor C may be configured to determine a resonant frequency in the resonant circuit 50A. In particular, the particulate matter detection unit 11 may use the first and second electrodes 321 and 322 to generate a capacitor.

A resonant frequency of the resonant circuit 50A may vary based on inductance of the coil L and inductance of the capacitor C. Therefore, when capacitance between the first and second electrodes 321 and 322 of the particulate matter detection unit 11 is changed, a resonant frequency of the resonant circuit 50A constituting the signal generator 12 may vary and a vibration frequency of a frequency signal generated by the signal generator 12 may vary.

Referring to FIG. 5B, a resonant circuit 50B with the signal generator 12 may include a transmitting resonant circuit 510 and a receiving resonant circuit 520. The respective resonant circuits 510 and 520 may include coils L1 and L2 and capacitors C1 and C2. In particular, the capacitor C1 may include the transmitting resonant circuit 510, and a capacitance may be generated by the first and second electrodes 321 and 322 of the particulate matter detection unit 11. A vibration frequency (e.g., resonant frequency) of the transmitting resonant circuit 510 may vary based on the inductance of the coil L1 and capacitance of the capacitor C1 generated by the first and second electrodes 321 and 322 of the particulate matter detection unit 11. Therefore, when capacitance between the first and second electrodes 321 and 322 of the particulate matter detection unit 11 is varied, a vibration frequency of a magnetic field that occurs in the transmitting resonant circuit 510 may also vary. Accordingly, a resonant frequency of the receiving resonant circuit 520 configured to generate a resonance by a reaction with a magnetic field of the transmitting resonant circuit 510 by a variation in the inductive coupling. Namely, the variation of the resonant frequency may be output to an output terminal of the signal generator 12.

The signal generator 12 may include an LC (inductor and capacitor) oscillation circuit (e.g. resonant circuit) that uses capacitance from the particulate matter detection unit 11 and may be configured to generate a frequency signal using the LC oscillation circuit. The LC oscillation circuit may be an oscillation circuit configured to use a LC resonance. An oscillation frequency of the LC oscillation circuit may be determined by inductance of a coil configured to generate LC resonance and capacitance of a capacitor.

When the signal generator 12 includes an LC oscillation circuit, a capacitor may be configured to be generated by the first and second electrodes 321 and 322 of the particulate matter detection unit 11 and may be used as a capacitor for LC resonance. Therefore, when capacitance between the first and second electrodes 321 and 322 of the particulate matter detection unit 11 varies, a resonant frequency of an LC oscillation circuit constituting the signal generator 12 may be varied and thus, a frequency characteristic of a frequency signal generated by the signal generator 12 may vary.

As described above, the signal generator 12 may include a resonant circuit or an oscillation circuit that uses capacitance between the first and second electrodes 321 and 322 of the particulate matter detection unit 11 and may be configured to output a frequency signal in which a frequency characteristic may vary based on capacitance between the first and second electrodes 321 and 322.

Referring again to FIG. 1, the frequency converter 13 may be configured to covert a frequency signal output from the signal generator 12 to a frequency area through Fast Fourier Transform (FFT). In other words, the frequency converter 13 may be configured to disassemble a frequency signal output from the signal generator 12 into frequency components. Each frequency component may be represented with a signal magnitude and a phase. The memory 14 may be configured to store an initial signal magnitude MO in a predetermined reference frequency. In particular, a reference frequency may represent a resonant frequency or an oscillation frequency of a frequency signal that occurs through the signal generator 12 at an initialization step. The initial signal magnitude may represent a signal magnitude in a resonant frequency or an oscillation frequency of a frequency signal that occurs through the signal generator 12 at an initialization step. Further, an initialization step may actuate the particulate matter sensor 10 in an idle state when a vehicle does not discharge an exhaust gas.

The detection result processor 15 may be configured to receive and analyze a result when a frequency is converted by the frequency converter 13 and may be configured to determine an exhaust level of a particulate matter. Further, the detection result processor 15 may be configured to operate the detection result output unit 16 based on an exhaust level of a particulate matter. When exhaust of a particulate matter increases by a malfunction or degradation of an exhaust gas control apparatus, the detection result output unit 16 may include a Malfunction Indicating Lamp (MIL) to provide an alert of the increase in exhaust of a particulate matter to a user.

Figure 6:
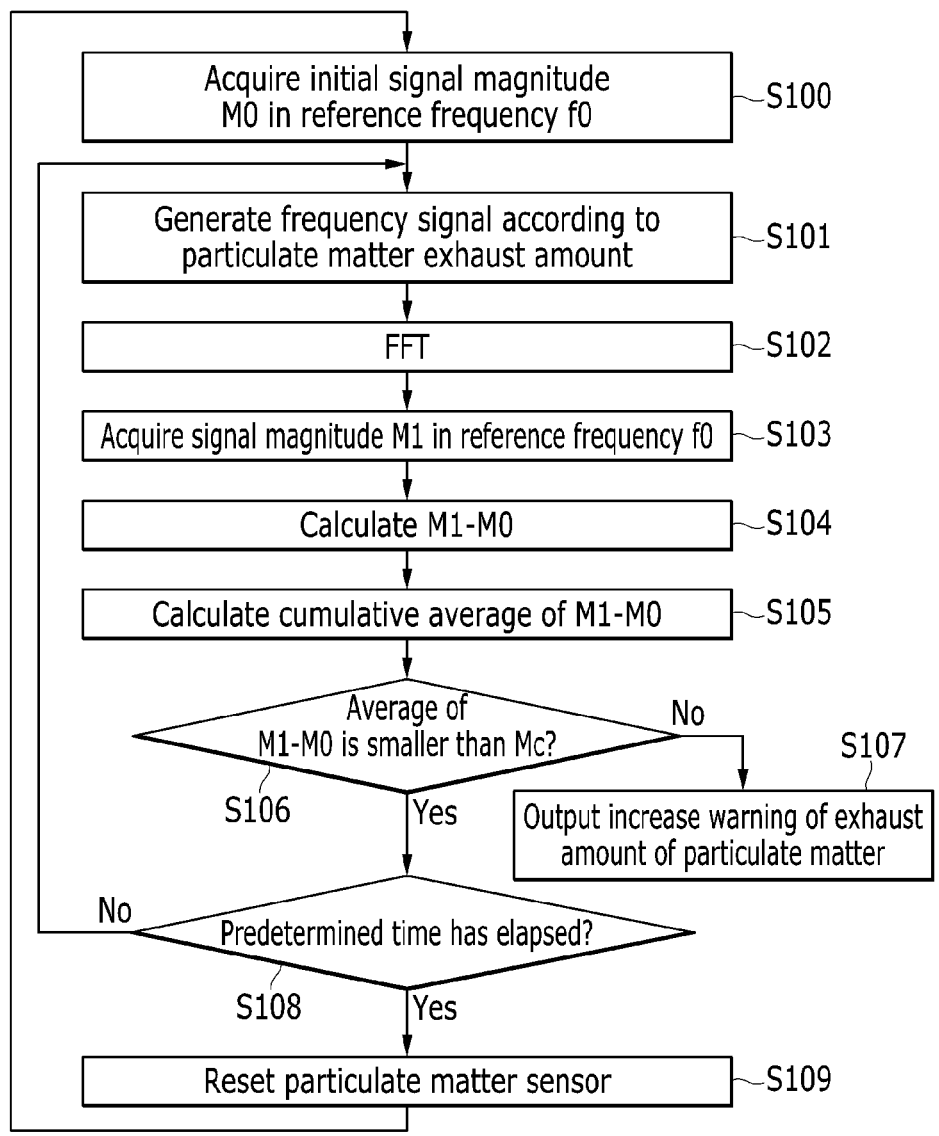
FIG. 6 is an exemplary flowchart illustrating a method of detecting a particulate matter of a particulate matter sensor according to an exemplary embodiment of the present invention.
Figure 7:
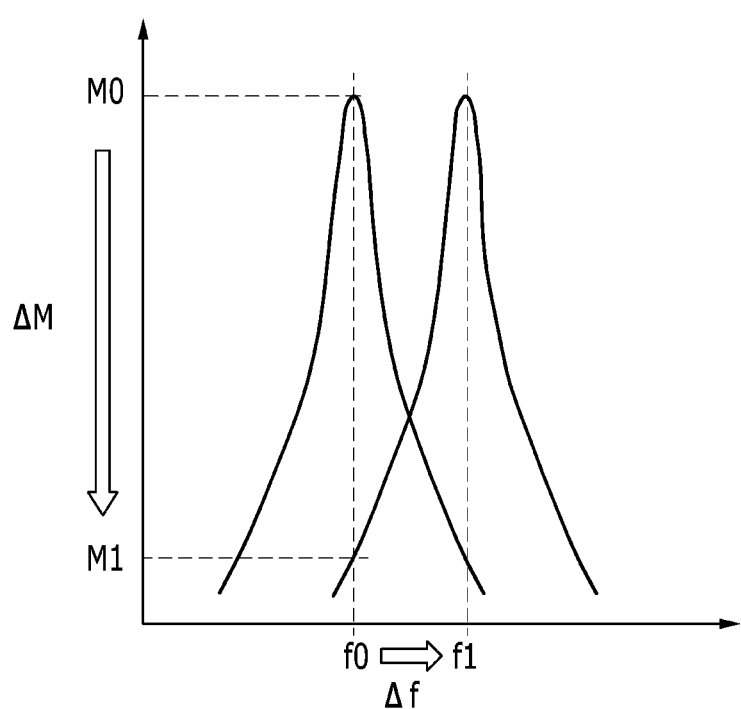
FIG. 7 is an exemplary graph illustrating an example in which a frequency characteristic of a frequency signal output from a signal generator varies based on a concentration of a particulate matter in a particulate matter sensor according to an exemplary embodiment of the present invention.

Hereinafter, a method of detecting a particulate matter in the particulate matter sensor 10 according to an exemplary embodiment of the present invention will be described with reference to FIGS. 6 and 7. FIG. 6 is an exemplary flowchart illustrating a method of detecting a particulate matter of a particulate matter sensor according to an exemplary embodiment of the present invention. FIG. 7 is an exemplary graph illustrating an example in which a frequency characteristic of a frequency signal output from a signal generator varies based on a concentration of a particulate matter in a particulate matter sensor according to an exemplary embodiment of the present invention.

Referring to FIGS. 6 and 7, the particulate matter sensor 10 according to an exemplary embodiment of the present invention may be configured to acquire an initial signal magnitude MO in a reference frequency f0 (S100). The particulate matter sensor 10 may be configured to acquire a resonant frequency of a frequency signal from the signal generator 12 as a reference frequency f0 produced in an idle state when a vehicle does not discharge an exhaust gas. The particulate matter sensor 10 may be configured to acquire a signal magnitude in the reference frequency f0 from a signal output from the signal generator 12 in an idle state and may be configured to determine the acquired signal magnitude to be an initial signal magnitude f0 in the reference frequency f0 (S100).

The acquired reference frequency f0 and an initial signal magnitude M0 in the reference frequency f0 may be stored at the memory 14. As an exhaust gas is discharged with driving of the vehicle, the particulate matter sensor 10 may be configured to generate a frequency signal based on a particulate matter exhaust amount using the particulate matter detection unit 11 and the signal generator 12 (S101).

As an exhaust gas flows within an exhaust line, disposed at the groove 311 between the first and second electrodes 321 and 322 of the particulate matter detection unit 11, a particulate matter may be collected and accumulated. Further, capacitance based on an accumulation amount of a particulate matter may occur between the first and second electrodes 321 and 322. The signal generator 12 may be configured to generate a frequency signal that corresponds to capacitance that occurs within the particulate matter detection unit 11. The signal generator 12 may include a resonant circuit or an LC oscillation circuit and may be configured to use the capacitance that occurs in the particulate matter detection unit 11 as capacitance to determine a resonant frequency in the resonant circuit or the LC oscillation circuit. Accordingly, the signal generator 12 may be configured to generate a frequency signal when a vibration frequency is determined by capacitance that occurs in the particulate matter detection unit 11 (S101).

A quantity of a particulate matter that accumulates at the groove 311 of the particulate matter detection unit 11 may vary based on a concentration of a particulate matter within an exhaust gas. Further, the capacitance that occurs in the particulate matter detection unit 11 may vary based on a concentration of a particulate matter within the exhaust gas. Therefore, a frequency characteristic of a frequency signal generated by the signal generator 12 may vary based on a concentration of a particulate matter within an exhaust gas. The frequency converter 13 may be configured to convert a frequency of a frequency signal output from the signal generator 12 using Fast Fourier Transform (FFT) (S102). The detection result processor 15 may be configured to acquire a signal magnitude M1 in a predetermined reference frequency f0 from a frequency conversion result output from the frequency converter 13 (S103). Thereafter, the detection result processor 15 may be configured to calculate difference values M1-M0 between a signal magnitude M1 (S103) and an initial signal magnitude M0 (S100-S104) and may be configured to calculate a cumulative average of the difference values M1-M0 (S105).

Thereafter, to distinguish an exhaust level of a particulate matter, the detection result processor 15 may be configured to compare an average of the difference values M1-M0 calculated (S105) with a predetermined threshold value Mc (S106). When an average of the difference values M1-M0 is equal to or greater than a threshold value Mc (S106), the detection result processor 15 may be configured to determine that an exhaust amount of the particulate matter is increased to a warning level. Accordingly, the detection result processor 15 may be configured to generate the detection result output unit 16 to output a warning output that provides a warning or notification of an increase of an exhaust amount of the particulate matter (S107). For example, the threshold value may be about 1 volt or about 10 dB.

When an average of the difference values M1-M0 is less than a threshold value Mc (S106), the detection result processor 15 may be configured to determine that there is no problem in an exhaust amount of the particulate matter. Accordingly, to calculate a next cumulative average, the detection result processor 15 may be configured to store an average of the difference values M1-M0 at the memory 14, and the particulate matter sensor 10 may be configured to repeat the previous determinations (S101 to S106).

The particulate matter sensor 10 may be configured to detection the particulate matter and determine whether a predetermined time has elapsed (S108). When a predetermined time has elapsed, the particulate matter sensor 10 may be reset, and particulate matters accumulated in the particulate matter detection unit 11 may be removed (S109). Reset of the particulate matter sensor 10 may include a process of removing particulate matters accumulated between the first and second electrodes 321 and 322. For example, heat may be applied to the particulate matter detection unit 11 using a heater (not shown).

A reset process may be performed to prevent an error that may occur when the particulate matter sensor 10 misinterprets an exhaust amount of a particulate matter to a warning level, for example when, a particulate matter is accumulated for a an extended duration in the particulate matter detection unit 11. When a particulate matter accumulated in the particulate matter detection unit 11 is removed through a reset process, the particulate matter sensor 10 may repeat the sampling processes (S100) and may be configured to acquire a reference frequency f0 and an initial signal magnitude M1 in the reference frequency f0. The particulate matter sensor 10 may continue to perform a particulate matter detection operation (S101 to S106).

As described above, the particulate matter sensor 10 according to an exemplary embodiment of the present invention may be configured to convert a capacitance variation based on a collection amount of a particulate matter to vary a resonant frequency. Further, an exhaust level of a particulate matter may be distinguished based on a level that a signal magnitude in a predetermined reference frequency changes based on a variation of a resonant frequency. Referring to FIG. 7, as a collection amount of a particulate matter varies, when capacitance of the particulate matter detection unit 11 varies, in a signal output through the signal generator 12, signal magnitudes M0 and M1 in resonant frequencies f0 and f1 and a specific frequency f0 may also vary.

In particular, a change of the width AM of the signal magnitudes M0 and M1 may be relatively largely represented, when compared with a change of the width in the resonant frequencies f0 and f1. In other words, even when the resonant frequencies f0 and f1 are adjusted with a minimal width, signal magnitudes M0 and M1 in the specific frequency f0may be adjusted with a greater width. Therefore, the particulate matter sensor 10 based on an exemplary embodiment of the present invention may be configured to accurately measure a particulate matter. For example, an exhaust level of a particulate matter may be distinguished based on a variation of signal magnitudes M0 and M1 in the specific frequency f0 instead of a frequency change and thus sensitivity thereof may be improved.

A method of detecting a particulate matter according to an exemplary embodiment of the present invention may be executed through software. When being executed with software, constituent elements of the present invention are code segments that execute a necessary work. A program or code segments may be stored at a processor readable medium or may be transmitted by a computer data signal that is coupled to a carrier in a transmitting medium or a communication network.

A computer readable recording medium includes an entire kind of record device that stores data that may be read by a computer system. A computer readable recording device may include, for example, a read-only memory (ROM), a random-access memory (RAM), a compact disc-ROM (CD-ROM), a digital versatile disk-ROM (DVD_ROM), a digital versatile disk-RAM (DVD_RAM), a magnetic tape, a floppy disk, a hard disk, and an optical data storage. Further, in the computer readable recording medium, codes that are distributed in a computer system connected to a network and in which a computer may read with a distributed method may be stored and executed.

While this invention has been described in connection with what is presently considered to be practical exemplary embodiments, it is to be understood that the invention is not limited to the disclosed exemplary embodiments, but, on the contrary, is intended to cover various modifications and equivalent arrangements included within the spirit and scope of the appended claims.

What is claimed is:

1. A particulate matter sensor, comprising:
   a particulate matter detection unit having first and second electrodes separately disposed on a substrate and configured to generate capacitance to correspond to a quantity of a particulate matter that accumulates between the first and second electrodes;
   a signal generator configured to generate a frequency signal in which a resonant frequency is determined by the capacitance; and
   a detection result processor configured to detect a signal magnitude of a predetermined reference frequency in the frequency signal and distinguish an exhaust level of the particulate matter based on a variation of the signal magnitude.

2. The particulate matter sensor of claim 1, wherein the particulate matter detection unit includes,
   a groove formed between the first and second electrodes where the particulate matter accumulates,
   wherein the capacitance is generated by the first and second electrodes and the particulate matter that accumulates between the first and second electrodes; and
   wherein the first and second electrodes are separately disposed at a first surface of the substrate.

3. The particulate matter sensor of claim 2, wherein the particulate matter detection unit is a Micro Electro Mechanical Systems (MEMS) structure.

4. The particulate matter sensor of claim 2, wherein the particulate matter detection unit further includes:
   a protective substrate coupled to a second surface of the substrate.

5. The particulate matter sensor of claim 1, wherein the signal generator includes:
   a resonant circuit configured to determine the resonant frequency by the capacitance and generate the frequency signal through the resonant circuit.

6. The particulate matter sensor of claim 1, wherein the signal generator includes:
   an LC oscillation circuit configured to determine the resonant frequency by the capacitance and generate the frequency signal through the LC oscillation circuit.

7. The particulate matter sensor of claim 1, further comprising:
   a frequency converter coupled between the signal generator and the detection result processor and configured to convert the frequency signal to a frequency area.

8. The particulate matter sensor of claim 1, wherein the detection result processor is configured to calculate a difference value between the signal magnitude and an initial signal magnitude in the reference frequency and configured to compare a cumulative average of the difference value with a predetermined threshold value to distinguish an exhaust level of the particulate matter.

9. The particulate matter sensor of claim 8, wherein the detection result processor is configured to acquire an initial signal magnitude in the reference frequency from a frequency signal output through the signal generator in an idle state.

10. The particulate matter sensor of claim 8, further comprising:
    a detection result output unit,
    wherein the detection result processor is configured to operate the detection result output unit to output an output that provides a warning of increase of an exhaust amount of the particulate matter, when a cumulative average of the difference value is equal to or greater than the threshold value.

* * * * *